United States Patent [19]

Hack et al.

[11] Patent Number: 4,725,139
[45] Date of Patent: Feb. 16, 1988

[54] METHOD AND APPARATUS FOR DETECTING DEFECTS IN TRANSPARENT MATERIALS

[75] Inventors: Hrabanus Hack, Mainz; Rainer Haspel, Monsheim, both of Fed. Rep. of Germany

[73] Assignee: Schott Glaswerke, Monsheim, Fed. Rep. of Germany

[21] Appl. No.: 731,785

[22] Filed: May 8, 1985

[30] Foreign Application Priority Data

May 17, 1984 [DE] Fed. Rep. of Germany ....... 3418283

[51] Int. Cl.$^4$ ............................................. G01N 21/88
[52] U.S. Cl. ..................................... 356/237; 250/563; 250/572; 356/239
[58] Field of Search ................ 356/237, 239; 250/562, 250/563, 572, 339, 341, 359.1

[56] References Cited

U.S. PATENT DOCUMENTS 4,297,587 10/1981 Baker ................................... 250/563
4,555,179 11/1985 Langerholc et al. ............ 356/237 X

FOREIGN PATENT DOCUMENTS 48644 3/1982 Japan ................................. 250/572

*Primary Examiner*—Davis L. Willis
*Assistant Examiner*—Matthew W. Koren
*Attorney, Agent, or Firm*—Quaintance, Murphy & Presta

[57] ABSTRACT

A method of detecting defects present at the surface and/or internally in transparent materials, particularly of detecting included foreign bodies or bubbles in glass, is disclosed. The test material is scanned with an electromagnetic radiation of a single wavelength which is set to the penetration depth in the test material. The intensity reflected by the defects is picked up and analyzed. By this method only defects located up to a specified depth in the material are detected. Visible light as well as UV- or IR radiation may be applied. The associated test rig comprises a tunable Laser (2), a conveyor belt (6) carrying the test material (5), a fast rotating mirror-wheel (3) which directs the light beam (4) at high speed over the test material (5), and an optical sensor (7) connected with an analyzer unit (8).

7 Claims, 6 Drawing Figures

METHOD AND APPARATUS FOR DETECTING DEFECTS IN TRANSPARENT MATERIALS

DESCRIPTION

The invention relates to a method of detecting defects located at the surface and/or internally, in transparent materials, in particular included foreign bodies or bubbles in glass, according to which the material which is to be tested is scanned by means of an electromagnetic radiation and the intensity of reflection by the defects is picked up and converted into an electrical signal and analyzed.

It is known that, for example, glass components or sheets of flat glass can be tested automatically at their surface for internal defects with the aid of a scanning light beam, preferably a laser beam. The light beam is passed over the test object and partially reflected at the surface thereof and partially allowed to pass therethrough. Any defects in the interior or at the surface of the test object disturb the reflected or transmitted beam. These disturbances are picked up by electro-optical methods and analyzed as fault signals. With this method it is easy to determine the position of a defect in relation to the length and breadth of the test object but not the depth at which the defect is located inside the object.

In various applications, including in particular the testing of objects of major thickness, it is necessary not only to obtain information about the presence of a defect but also to know how deep this is situated inside the material, that is to say, at what distance from the surface of the object. The case may also arise where the search for defects is to cover only a certain depth, or where defects at relatively different depths are to be differently evaluated.

The objective of the present invention therefore resides in a method and a test rig enabling the determination of the distance of the defects from the surface of the tested material.

This objective is achieved by means of a method and a test rig according to the claims.

The method according to the invention makes use of the fact that the depth of penetration of electromagnetic radiation into the tested material depends on the wavelength.

The penetration depth E is defined as the reciprocal value of the absorption coefficient K:

$$E = 1/K \text{ (cm)} \tag{1}$$

$$K = \left[\frac{2.3}{d}\right]\left[\log\left(\frac{1}{Ti}\right)\right] \text{ (cm}^{-1}\text{)} \tag{2}$$

d = material thickness (cm)
Ti = pure transmission
Ti = (T/P)
T is the transmission, P the reflection factor.
1 = P specifies how much intensity is reflected at the surfaces.

The penetration depth is not sharply defined. Where a homogenous material can be assumed to be involved, the intensity at single penetration depth has dropped to 37% of the initial intensity, at double penetration depth to 13.5% and at triple depth to 5% of the applied intensity.

This penetration depth is hereinafter called the test depth.

Adjustment or variation of test depth in accordance with the present invention is made as follows:

Objects which appear transparent to the human eye are permeable in respect of electromagnetic rays with wavelengths between 380 and 780 nm. This is the visible light region. Such objects also always have regions in the spectrum of the electromagnetic radiation in which they are not, or are to a weaker degree, permeable relative to electromagnetic radiation, that is to say the transmission of the radiation concerned is more or less strongly reduced in these regions.

Between the regions of good and poor transmission there is a transitional region in which transmission decreases steadily. The variation of transmission as a function of wavelength in this transitional region can be precisely covered by measuring technology. It is therefore always possible to find a wavelength for the scanner light of the testing device according to the invention which would then generally come from the invisible ultraviolet or infrared region of the spectrum which is associated with a very specific desired transmission. On the other hand, a specific penetration depth of the light in the said object also corresponds to a specific transmission. In this fashion it is possible, through the wavelength of the scanner light, to select the penetration depth which determines the depth of testing. According to the invention this allows fault-testing not only of objects which are transmissive in respect of visible light whilst being non-transmissive in other regions but also of objects which are non-transmissive in the visible region but have good transmission in another region.

In a fault-detection by means of the testing device according to the invention, the light of the scanner beam must first penetrate into the test material and then return along the same path after having been scattered or reflected at the fault. Depending on the sensitivity of the opto-electronic array and on the magnitude of the defect, it will therefore be possible to find faults located up to one to two times the penetration depth inside the material. That will then be the above-described test depth. Defects located deeper than this will no longer provide an optical signal and will not be registered.

The test depth can be still more sharply defined if weak signals caused by defects in deeper layers of the tested material are cut off by means of an electronic threshold and thus disregarded in the analysis.

Defects which are located at a greater distance from the surface than the test depth generate no optical signal and will not show up. By passing the object several times through the test rig according to the invention or through a series of successively arranged test rigs according to the invention and varying test depth in appropriate manner between the individual test passes, it is possible to associate detected faults with specific depth layers in the object.

A special application of the present invention resides in operating the test rig with scanner light of a selected wavelength which cannot at all penetrate into the transparent test object. In this fashion defects at the surface of the object are shown up by means of the reflected light completely uninfluenced by defects which are located inside the object.

Examples of embodiments of the invention are hereinafter more particularly described with reference to the drawings in which.

Figure 1:
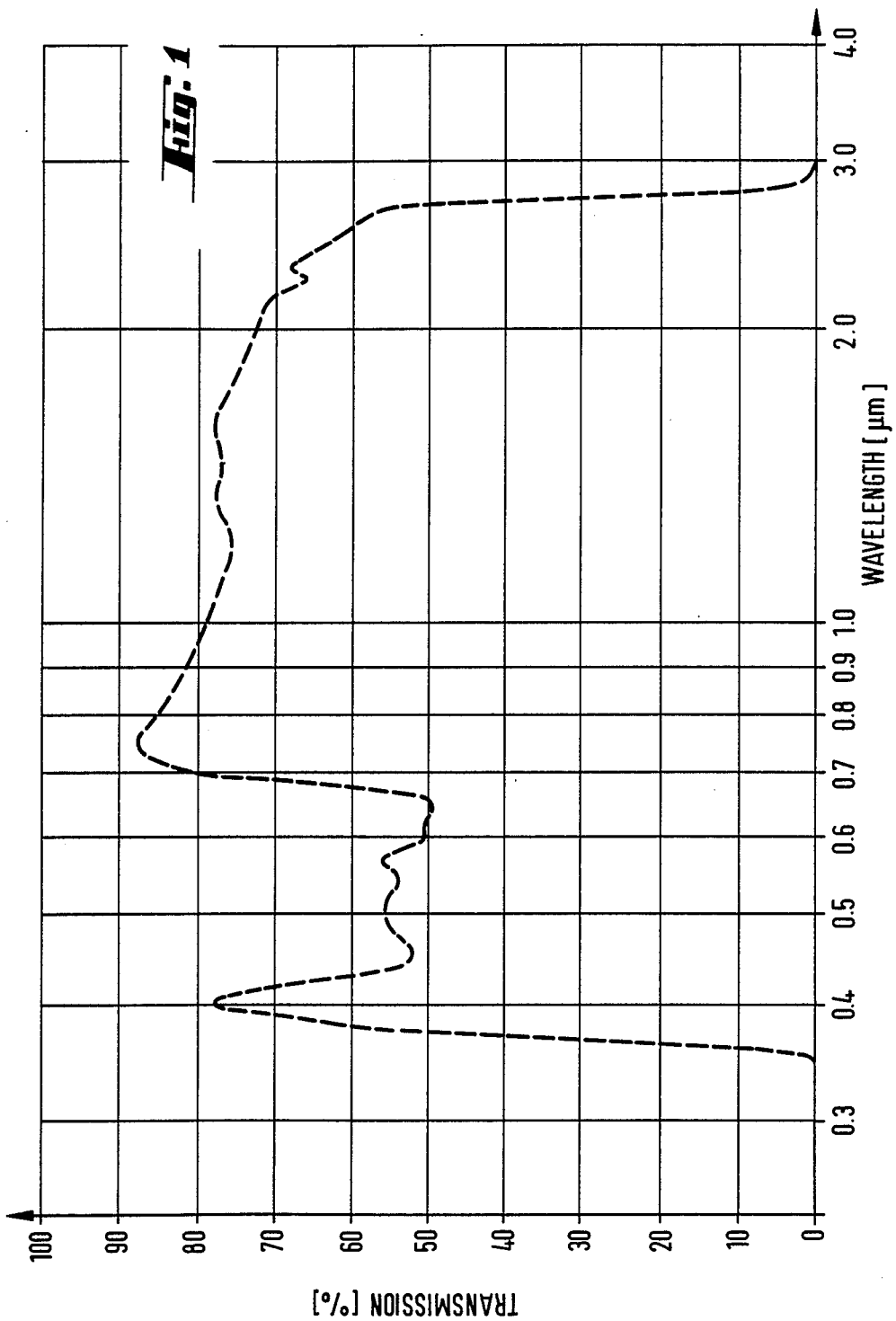
FIG. 1 is a diagram of radiation transmission degree of television screen glass 8209, thickness 11 mm, in relation with wavelength.
Figure 2:
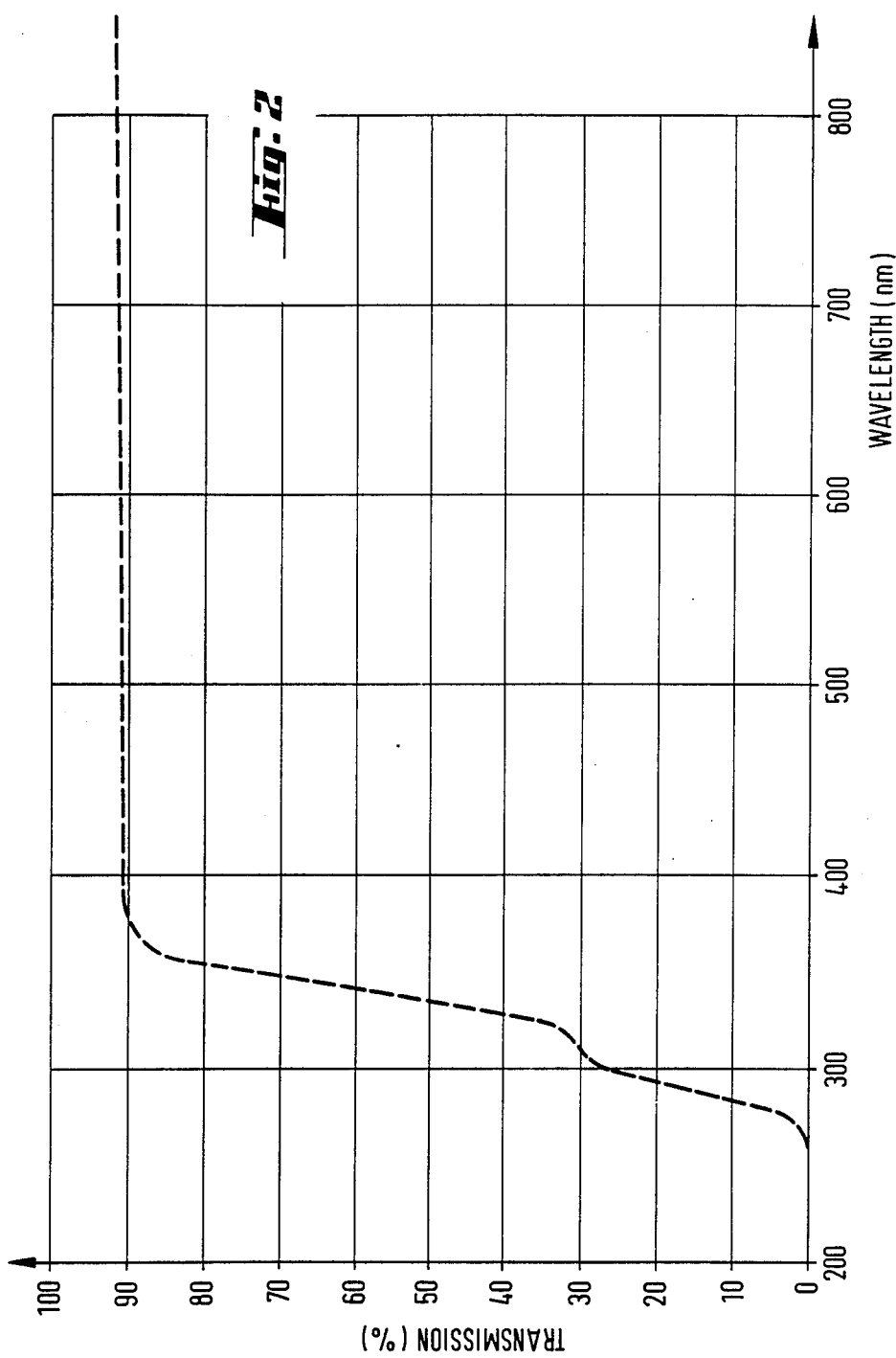
FIG. 2 is a diagram of the degree of radiation transmission of television screen glass 8209, thickness 0.17 mm, in relation with wavelength.

In television screens, bubbles located on the surface of the inside contour of the screen and closely thereebeneath constitute a special defect characteristic which ought to be picked up separately from all other faults. The television screen glass type 8209 has good transparency between 370 and 3700 nm. In a thickness of 11 mm, it is non-transmissive 350 nm (FIG. 1). FIG. 2 shows that for a thickness of 0.17 mm on the other hand it still has a measurable transmission down to 270 nm.

Figure 3:
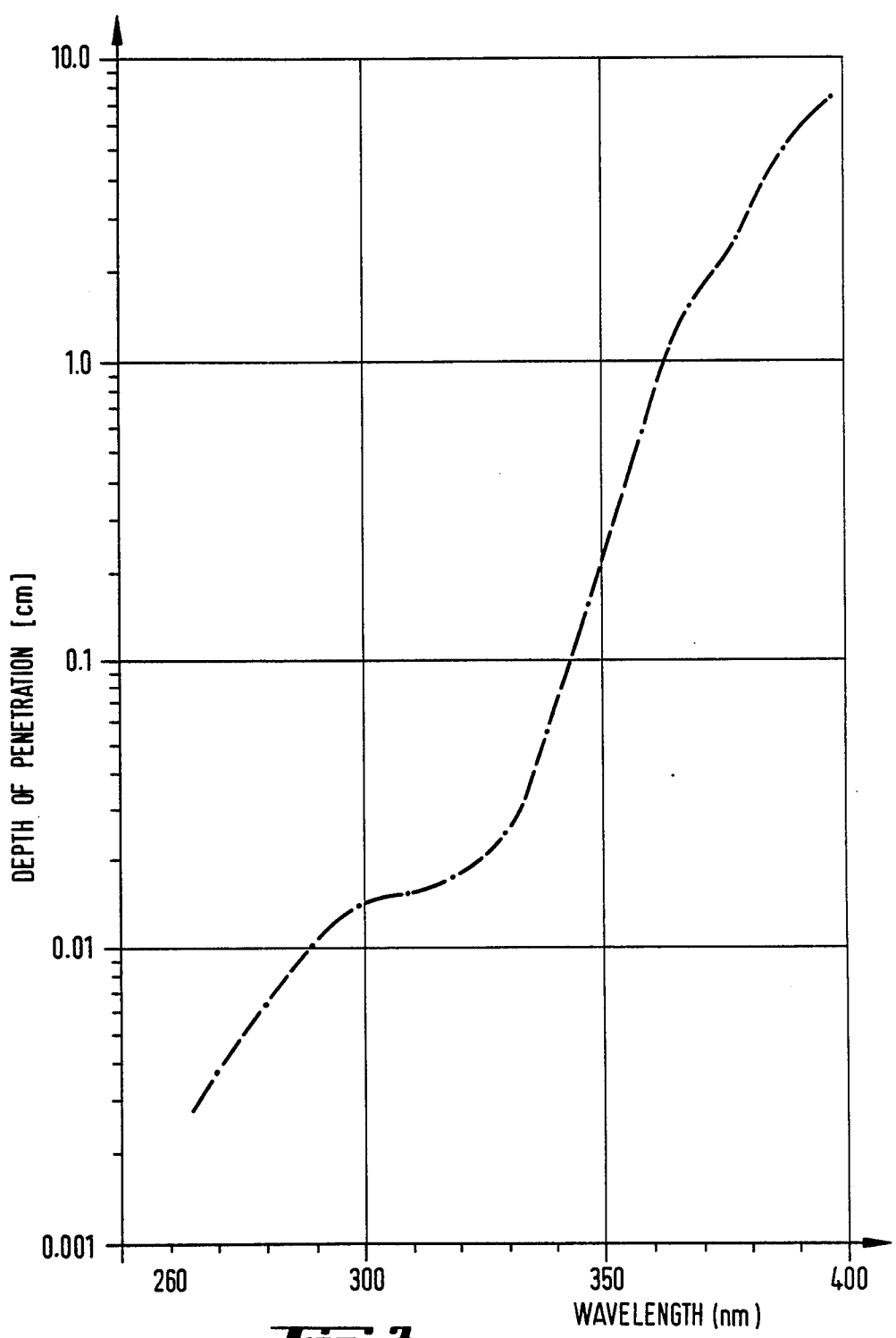
FIG. 3 is a diagram of the penetration depth of radiation in television screen 8209 in relation with wavelength.
Figures 4, 5:
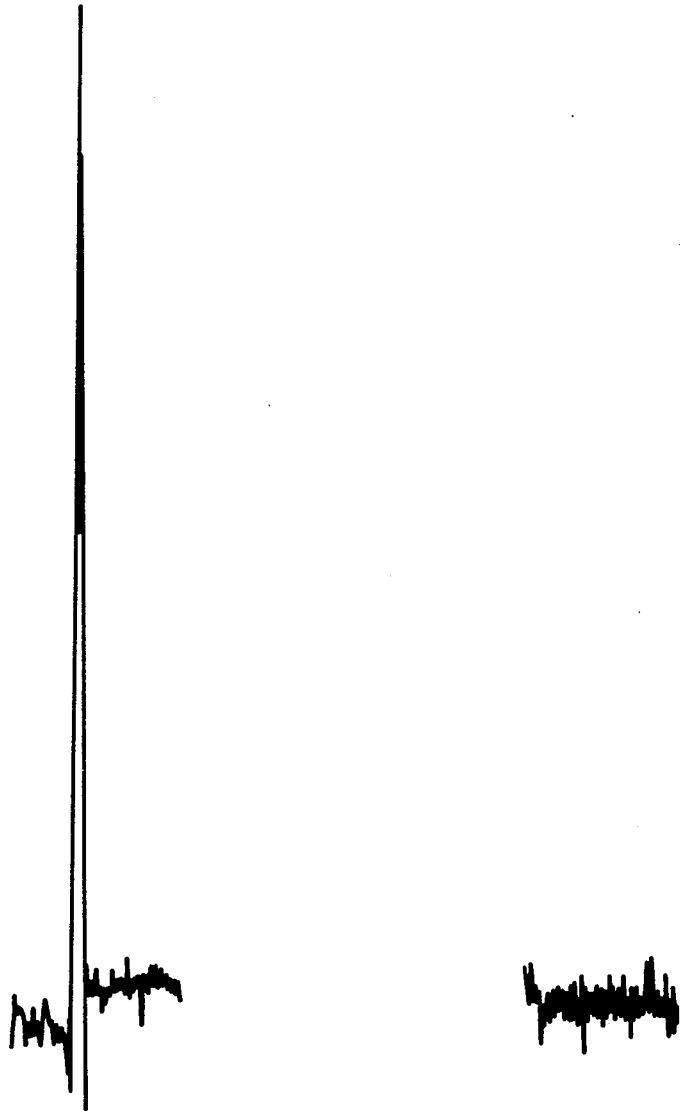
FIG. 4 shows the signal of the optical sensor during the scanning of a bubble located 0.1 mm below the surface of a television screen, operating with light at wavelength 314 nm.
FIG. 5 shows the signal of the optical sensor scanning a bubble located at 3 mm below the surface of a television screen, operating with light at wavelength 314 nm.

In this transitional region between 270 and 370 nm, which is known as the UV-edge, transmission, and with it the penetration depth, varies very strongly with wavelength (FIG. 3). Here any desired penetration depth may be found by selection of a specific wavelength and application of equations (1) and (2). In our example, we selected a wavelength of 314 nm which for a layer thickness of 0.17 mm has a transmission of 31% and a pure transmission of 33.7%. This corresponds to a penetration depth of 0.156 mm. With a monochromatic radiation of the said wavelength, we solved the problem of picking up bubbles only at and closely beneath the surface of a television screen. To this end, the emission line was filtered out at 314 nm from the spectrum of an Hg-high pressure lamp, the television screen was scanned with this light and the light which was reflected by the screen was analyzed. FIGS. 4 and 5 show two examples of the potential curve of the optical sensor during the scanning of two bubbles in the screen. In FIG. 4, a marked potential peak (signal) is clearly observable which was caused by a bubble located 0.1 mm below the surface of the screen. In FIG. 5, a bubble located 3 mm below the surface was scanned by the sensor. No signal was recorded in this case, which corresponds to the present invention. By comparison, the screen was scanned in conventional manner with visible light. Here the more deeply located bubbles generated a signal in the same way as those which were located closely beneath the surface.

Figure 6:
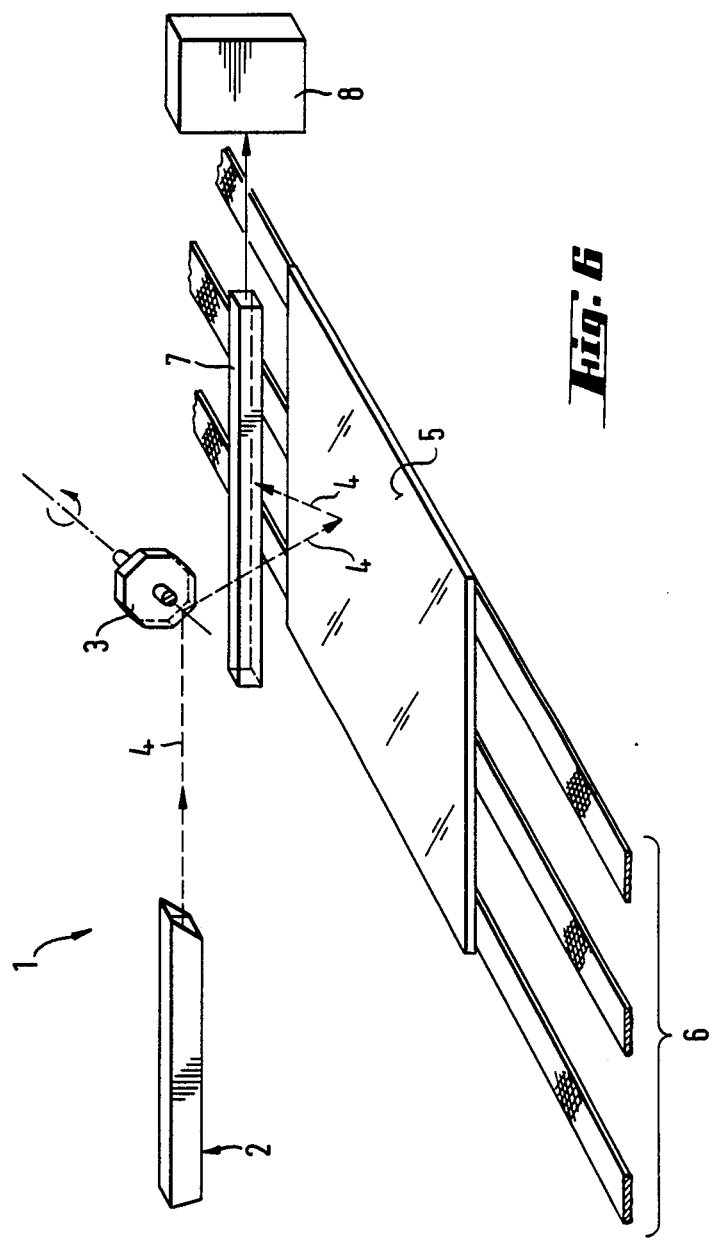
FIG. 6 illustrates a test rig according to the invention.

FIG. 6 shows a test rig according to the invention for detecting defects. The test rig 1 comprises a light source 2 which is a Laser emitting light at a wavelength which has the desired penetration depth in the transparent test material. Conveniently, a laser is used for this purpose which allows the wavelength of emitted light to be freely selected within certain limits (a so-called tunable laser). The laser 2 directs its light at a rapidly rotating mirror wheel 3 whereby the laser beam 4 is passed at high speed over the transparent test object 5. The object is conducted on a conveyor belt 6 beneath the test rig/array. An optical sensor 7 spaced above the test object picks up the light which is encountered by the defects and reflected in the object. The signals of the optical sensor are registered in an analyzer unit 8.

What is claimed is:

1. A method of detecting defects in a test material by the use of incident electromagnetic radiation which is incident on the test material comprising the steps of:
   I. selecting the wavelength of the incident electromagnetic radiation such that defects of the test material within a characteristic penetration depth of said incident electromagnetic radiation is scattered such that the scattered electromagnetic radiation will reach a detector; and
   II. scanning the test material with the incident electromagnetic radiation thus selected; and
   III. detecting the scattered electromagnetic radiation from defects in said test material by use of the detector; and
   whereby, when the incident electromagnetic radiation is scanned relative to the test material the detector will receive a sensible variation in the intensity of the scatterd electromagnetic radiation in accordance with the presence of defects within the characteristic penetration depth.

2. Method according to claim 1, characterised in that the incident electromagnetic radiation has a wavelength within the visible region of the electromagnetic spectrum.

3. Method according to claim 1, characterised in that the incident electromagnetic radiation has a wavelength within the invisible region of the electromagnetic spectrum.

4. Method according to claim 3, characterised in that the incident electromagnetic radiation has a wavelength within the ultraviolet region.

5. Method according to claim 3, characterised in that the incident electromagnetic radiation has a wavelength within the infrared region.

6. Method according to claim 1, characterised in that the incident electromagnetic radiation has a wavelength in respect to which the test material has reduced transmissivity.

7. Method according to claim 1, characterised in that the test material is successively scanned by incident electromagnetic radiation of different wavelengths.

* * * * *